US009513203B2

(12) United States Patent
Kulkarni et al.

(10) Patent No.: US 9,513,203 B2
(45) Date of Patent: Dec. 6, 2016

(54) METHODS FOR PREDICTING DYNAMIC SAG USING VISCOMETER/RHEOMETER DATA

(75) Inventors: Sandeep Kulkarni, Pune Maharashtra (IN); Sharath Savari, Hyderabad Andhrapradesh (IN); Kushabhau D. Teke, Maharashtra (IN); Dale E. Jamison, Houston, TX (US); Robert J. Murphy, Houston, TX (US); Anita Gantepla, Karnataka (IN)

(73) Assignee: Halliburton Energy Services, Inc., Houston, TX (US)

( * ) Notice: Subject to any disclaimer, the term of this patent is extended or adjusted under 35 U.S.C. 154(b) by 1138 days.

(21) Appl. No.: 13/492,885

(22) Filed: Jun. 10, 2012

(65) Prior Publication Data
US 2013/0332089 A1 Dec. 12, 2013

(51) Int. Cl.
*G01N 11/00* (2006.01)
*G06F 19/00* (2011.01)
*G01N 15/04* (2006.01)

(52) U.S. Cl.
CPC .............. *G01N 15/04* (2013.01); *G01N 11/00* (2013.01)

(58) Field of Classification Search
CPC .................................. G01N 15/04; G01N 11/00
USPC .......................................................... 702/50
See application file for complete search history.

(56) References Cited

U.S. PATENT DOCUMENTS

| 2,845,793 A | 8/1958 | Cartwell, Jr. |
|---|---|---|
| 6,330,826 B1 | 12/2001 | Heeten |
| 6,584,833 B1 | 7/2003 | Jamison |
| 6,931,916 B2 | 8/2005 | Zamora |
| 7,870,782 B2 | 1/2011 | Tehrani |
| 8,024,962 B2 | 9/2011 | Tonmukayakul et al. |
| 2003/0084717 A1 | 5/2003 | Herzhaft et al. |
| 2004/0261507 A1 | 12/2004 | Zamora et al. |
| 2011/0167901 A1 | 7/2011 | Jamison |
| 2011/0219856 A1 | 9/2011 | Tonmukayakul |

FOREIGN PATENT DOCUMENTS

WO  2013188124 A1  12/2013

OTHER PUBLICATIONS

ASME, Drilling Fluids Processing Handbook, 2005, Gulf Proffesional Publishing, p. 33-36.*
R. P. Chhabra, Bubbles, drops and particles in non-Newtonian fluids, Taylor & Francis, New York (2007).
R.B. Bird, W. E. Stewart & E. N. Lightfoot, Transport Phenomena, Wiley, New York (1960).
D. De Kee & R.P. Chhabra, Transport Processes in Bubbles, Drops, and Particles 2nd Ed, Taylor & Francis (2002).
N. Tonmukayakul, J. E. Bryant, M. S. Talbot and J. F. Morris, Dynamic and Steady Shear Properties of Reversibly Cross-linked Guar Solutions and Their Effects on Particle Settling Behavior, Society of Rheology conference, Monterey CA, Aug. 3-8, 2008.

(Continued)

*Primary Examiner* — John Breene
*Assistant Examiner* — Peter Ngo
(74) *Attorney, Agent, or Firm* — McDermott Will & Emery LLP; Tenley Krueger

(57) ABSTRACT

A method for quantitatively determining dynamic barite sag in drilling fluids includes measuring rheological properties with viscometers and/or rheometers, and introducing the parameters into an equation to obtain the sag rate.

6 Claims, 2 Drawing Sheets

(56) References Cited

OTHER PUBLICATIONS

Atapattu et al., "Creeping sphere motion in Herschel-Bulkley fluids" (1995).

Baroid Fluid Services, DHAST Dynamic High Angle Settling Test Service Analyzes Potential for Sag, 2006.

Hanson et al, Investigation of barite sag in weighted drilling fluids in highly deviated wells, SPE 20423 (1990).

Arild Saasen, Sag of weight materials in Oil based Drilling fluids, IADC/SPE 77190 (2002).

Murphy et al, Apparatus for Measuring the Dynamic Solids-Settling Rates in Drilling Fluids, SPE 103088 (2006).

P. R. Paslay et al, A phenomenological approach to Analysis of barite sag in Drilling Muds, SPE 110404 (2007).

N. Tonmukayakul, J. E. Bryant, M. S. Talbot and J.F. Morris, Dynamic and Steady Shear Properties of Reversibly Cross-Linked Guar Solutions and Their Effects on Particle Settling Behavior, Society of Rheology conference, Monterey CA, Aug. 3-8, 2008.

P. A. Bern et al., Field Monitoring of Weight-Material Sag, AADE (2010).

Paul D. Scott et al, Barite Sag management: Challenges, strategies and opportunities, IADC/SPE 87136 (2004).

P. A. Bern et al., The influence of drilling variables on barite sag, SPE 36670 (1996).

International Search Report and Written Opinion for PCT/US2013/043374 dated Oct. 4, 2013.

V. Tirtaatmadja, P. H. T. Uhlherr & T. Sridhar, Creeping Motion of Spheres in Fluid, Journal of Non-Newtonian Fluid Mech., 35, 327 (1990).

M. J. Solomon and S. J. Muller, Flow Past a Sphere in Polystyrene-based Boger Fluids: the effect on the drag coefficient of finite extensibility, solvent quality and polymer molecular weight, Journal of Non-Newtonian Fluid Mech., 62, 81 (1996).

Jamison and Clements, A new test method to characterize settling/sag in drilling fluids in extended reach drilling, Drilling Tech Symposium, 27, 109 (1990).

A. E. Boycott, Sedimentation of Blood Corpuscles, Nature, 104, 532 (1920).

D. T. Jefferson, New Procedure Help Monitor Sag in the Field, paper ASME 91 PET 3, Energy Sources technology conference and exhibition, New Orleans, Jan. 20-24, 1991.

D. V. Boger, Dilute inter-relations between processing, structure and properties of polymeric materials, Elsevier, Amsterdam (1984).

R. Murphy, D. Jamison, T. Hemphill, S. Bell, C. Albrecht, Measuring and Predicting Dynamic Sag, SPE Drilling & Completion, 142-149, Jun. 2008.

\* cited by examiner

Plot of Predicted Sag rates vs. Experimental sag rates [$k = 0.18$]

Plot of Predicted Sag rates [$\alpha$ = 0.00126, $\beta$ = 0.75] vs. Experimental sag rates of fluids

METHODS FOR PREDICTING DYNAMIC SAG USING VISCOMETER/RHEOMETER DATA

CROSS-REFERENCE TO RELATED APPLICATIONS

None.

FIELD

The present invention generally relates to methods for characterizing dynamic sag in fluids containing particulate material, especially wellbore servicing fluids containing a particulate weighting material.

BACKGROUND

Drilling fluid, also known as "mud", is used in the drilling of subterranean wells, and assists in the drilling operation in several ways, including by removing rock cuttings from the wellbore to the surface, by cooling and lubricating the drill bit, and providing a hydrostatic head to maintain the integrity of the wellbore walls and prevent well blowouts.

Drilling fluids can be formulated in a number of ways known in the art. A drilling fluid typically comprises water and/or oil or synthetic oil or other synthetic material or synthetic fluid as a base fluid, with solids in suspension. A non-aqueous based drilling fluid typically contains oil or synthetic fluid as a continuous phase and may also contain water dispersed in the continuous phase by emulsification so that there is no distinct aqueous layer in the fluid. Such a dispersion is generally referred to as an invert emulsion, water-in-oil emulsion, or oil based mud (OBM).

The density of the drilling mud is closely maintained in order to control the hydrostatic pressure that the mud exerts at the bottom of the well. It is common for a drilling fluid to include a weighting material, or weighting agent, to increase the density of the drilling fluid. Barite is the most common weighting material, although others, including hematite, are used.

Particulates in a suspension, such as a weighting material in a drilling fluid, are prone to a type of settling referred to as "sag" or "barite sag", in which barite particles accumulate and cause variation in density throughout the drilling fluid. Barite sag can occur at dynamic conditions at low levels of shear rates, for example, during drill pipe rotation, or when running casing or logging tools.

The large density variations created by sag can create wellbore management problems, and can even result in wellbore failure. Additionally, fluid sag can lead to sticking of drill pipe, difficulty in re-initiating and/or maintaining proper circulation of the fluid, possible loss of circulation and disproportionate removal from the well of lighter components of the fluid. Barite sag is of particular concern in oil-based drilling fluids that are typically used in moderate and high pressure/temperature environment. Barite sag is also of concern in highly deviated, directional and ERD (extended reach drilling) wells, and experiments have shown that the greatest influences of barite sag occur at well bore inclinations from 40° to 60°.

Predicting and controlling barite sag has been difficult, as the influence of fluid rheology on dynamic sag is not quantitatively established. DHAST or Dynamic High Angle Sag Tester by FANN Instrument company, which is disclosed in the patent U.S. Pat. No. 6,584,833 to Jamison and Murphy, which is incorporated by reference herein, is an instrument that can measure the rate of particle settling to indicate the sag rate; however, this device has the disadvantage that it must be used in a laboratory setting and cannot be used in the field. Further, the DHAST method requires labor of about 2 man-hours per test and the test runs for a period of 15-18 hours.

Methods of predicting sag in the field have included variations of a viscometer sag test, in which drilling fluid is sheared inside a heat cup or well, and is subsequently analyzed for changes in density. In such tests, sag tendency is considered to be proportional to the change in density, but such tests do not provide a quantitative measure of the dynamic sag rate.

Thus, a need exists for a quantitative method of predicting sag based on available rheological properties of the fluid.

SUMMARY

The present invention, in its many embodiments, is a method for quantitatively predicting dynamic barite sag, based on rheological properties of the fluid measured by a viscometer and/or rheometer. The rheological properties are introduced into an equation to determine the dynamic sag rate.

In one embodiment, the invention is a method of predicting the sag rate for a particulate suspended in a fluid. In an embodiment, the fluid is a drilling fluid, and the particulate is a weighting material. In an embodiment, the weighting material is barite.

The Rheological data from a viscometer/rheometer may be obtained in terms of shear stress and/or viscosity at desired conditions of shear rate ($\gamma$), temperature (T) and pressure (P). Considering the shear-thinning characteristic of the drilling fluids, pseudo-plastic models including power-law model, Eyring model, Cross model, Carreau model, Ellis model or the like may be applied to the Rheology data to extract the characteristic parameters. In addition, the Rheology data may also be modeled considering the existence of yield stress (or apparent yield stress), i.e., using visco-plastic models. Different visco-plastic models may include Bingham-plastic model, Casson model, Herschel-Bulkley model or the like. The Rheological properties of the fluid that comprise of Rheological data and/or the characteristics parameters obtained by applying one or more of above pseudo-plastic/visco-plastic models are used in an equation to predict the sag rate behavior.

In one embodiment, the rheological properties include viscosity and visco-plastic characteristics from Herschel-Bulkley model in terms of yield stress, and shear thinning index. The viscosity, yield stress, and shear-thinning index can be obtained from a conventional (constant shear rate concentric cylinder viscometer/rheometer with an "API" geometry) viscometer/rheometer. In embodiments the conventional viscometer/rheometer can be a Fann®-35, fann-50, fann-75, or fann-77 viscometer/Rheometer.

In an embodiment the present invention illustrates that Gravitational Force=Viscous Drag+Visco-plastic Drag to describe settling behavior of barite in drilling fluids. An example of this is shown in the equation that can be used with such rheological information is:

$$(4/3)*\pi*a_i^3*(\rho_s-\rho_f)*g = 6*\pi*a_i*U_i*(\mu+k*(\tau_0^{HB})^{1/n})$$

where $a_i$ is the radius of the weighting material particle, $\rho_s$ is the density of the weighting material particle, $\rho_f$ is the density of the fluid surrounding the particle, g is the acceleration due to gravity, $U_i$ is the dynamic sag rate or vertical velocity of the sagging particle of size $a_i$, $\mu$ is the viscosity of the drilling fluid, k is an empirical constant that that can range from 0.01 to 10 when the terms in the equation are in SI units, $\tau_0^{HB}$ is the yield stress, and n is the shear thinning index. The rheological properties are obtained at desired conditions of shear rate ($\gamma$), temperature (T) and pressure (P).

In addition to shear stress or viscosity data from a viscometer/rheometer, the visco-elastic data may be obtained from a rheometer at desired conditions of temperature (T) and pressure (P). The visco-elastic data may be in terms of first Normal stress difference, second normal stress difference, primary normal stress coefficient, second normal stress coefficient, elongational viscosity, the dimensionless visco-elastic parameters including Maxwellian relaxation time, Deborah number, Weissenberg number, elasticity number and the like.

The Rheological properties of the fluid that comprise of Rheological data and/or the characteristics parameters obtained by applying one or more of above pseudo-plastic/visco-plastic models and/or the above obtained visco-elastic properties are used in a equation to predict the sag rate behavior.

An embodiment includes a method of predicting the dynamic sag rate of a weighting material in a drilling fluid by obtaining rheological data from a rheological measuring device and introducing the rheological properties into an equation to determine the dynamic sag rate where the rheological properties comprises the viscosity of the fluid surrounding the weighting material and first Normal stress difference, optionally the rheometer is an Anton Paar rheometer.

In one embodiment, the rheological properties include the viscosity of the fluid surrounding the weighting material and visco-elastic properties that may comprise of first Normal stress difference that is defined as follows. For a viscoelastic fluid under flow, normal stresses in velocity and velocity gradient directions, $\tau_{xx}$ and $\tau_{yy}$, respectively, may become unequal and the difference ($\tau_{xx}-\tau_{yy}$) is defined first Normal stress difference $N_1$. The viscosity of the fluid surrounding the weighting material can be obtained using a conventional viscometer/rheometer, such as a fann-35 viscometer/rheometer. The first Normal stress difference can be obtained using arheometer, such as an Anton Paar rheometer. The settling behavior of barite in drilling fluids could be described as Gravitational Force=Viscous Drag+Visco-elastic Drag. An example of this is shown in the equation that can be used with such rheological properties is:

$$(4/3)*\pi*a^3*(\rho_s-\rho_f)*g=6*\pi*\eta*a*U+\alpha*4*\pi*a^2*|N_1|^\beta$$

where a is the average radius of the weighting material particle, $\rho_s$ is the density of the weighting material particle, $\rho_f$ is the density of the fluid surrounding the particle, $\eta$ is the viscosity of the fluid surrounding the weighting material, $\alpha$ is an empirical constant ranging from 0.0001 to 0.1, $|N_1|$ is the absolute value of the first Normal stress difference, and $\beta$ is an empirical constant ranging from 0.5 to 1.5. The rheological properties are obtained at a given condition of shear rate ($\gamma$), temperature (T) and pressure (P).

DETAILED DESCRIPTION

Figure 1:
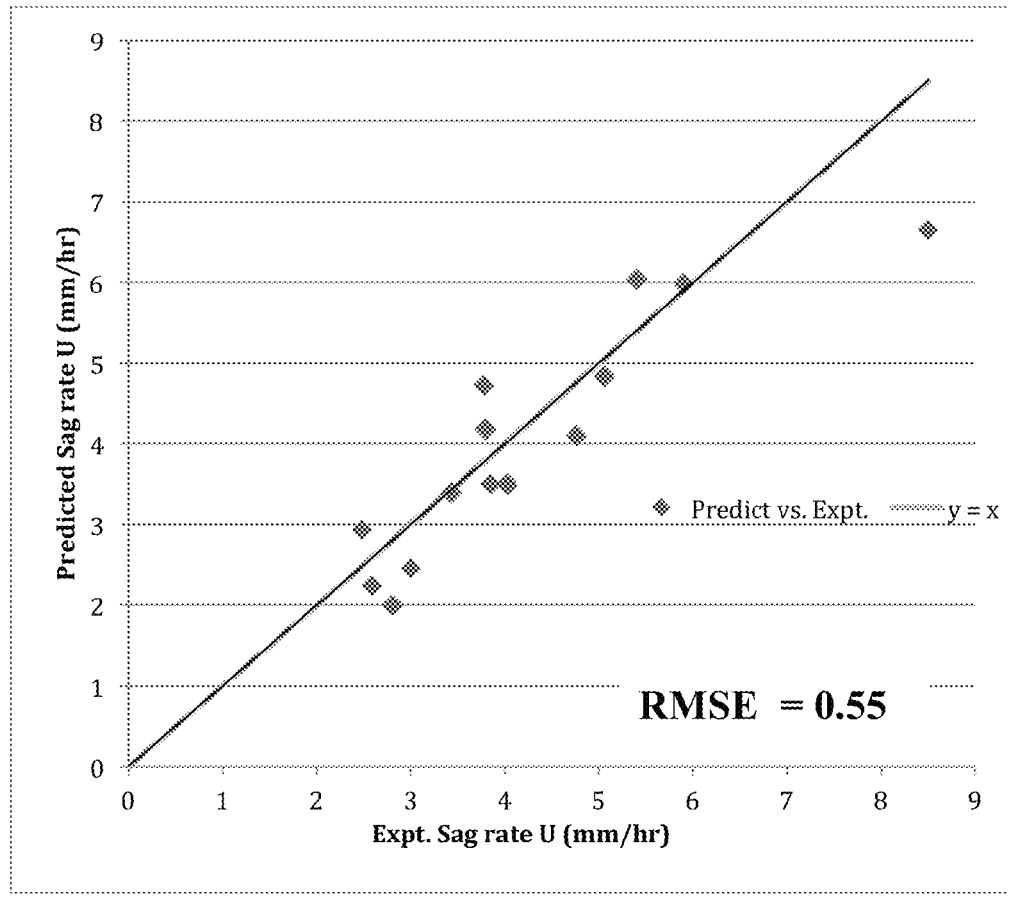
FIG. 1 is a plot of sag rate predicted by Equation 2 versus experimental sag as determined by DHAST, for various drilling fluids.

Disclosed herein is a method of determining the dynamic sag rate of a drilling fluid using data gathered from viscometer and/or rheometer that can be used at a drilling site or in a lab.

The Rheological data from a viscometer/rheometer may be obtained in terms of shear stress and/or viscosity at desired conditions of shear rate ($\gamma$), temperature (T) and pressure (P). Considering the shear-thinning characteristic of the drilling fluids, pseudo-plastic models including power-law model, Eyring model, Cross model, Carreau model, Ellis model or the like may be applied to the Rheology data to extract the characteristic parameters. In addition, the Rheology data may also be modeled considering the existence of yield stress (or apparent yield stress), i.e., using visco-plastic models. Different visco-plastic models may include Bingham-plastic model, Casson model, Herschel-Bulkley model or the like. The Rheological properties of the fluid that comprise of Rheological data and/or the characteristics parameters obtained by applying one or more of above pseudo-plastic/visco-plastic models are used in an equation to predict the sag rate behavior.

In one embodiment, the method includes the steps of measuring viscosity, and visco-plastic properties that may comprise of yield stress, and shear thinning index of a drilling fluid using a viscometer/rheometer, and determining the dynamic sag rate via an equation that quantitatively establishes the relationship between those rheological parameters and sag rate. The viscometer/rheometer can be many known in the art, especially those that can be used at drilling sites. Examples of possible conventional viscometers/rheometers include the Fann Instrument Company's Fann Model 35, Fann Model 75, and Fann Model 77. The equation can be Equation 2, which is described below.

One feature of the present invention is that conventional viscometers/rheometers, such as the Fann® viscometers/rheometers, can be used in the field, and are not confined to the laboratory. Determining barite sag in the field can be more convenient and cost-effective over methods that require the use of laboratory instruments. Additionally cost-effectiveness in the laboratory can be improved by a reduction in the number of trial and errors needed can reduce time and costs.

Equations were derived to model barite sag behavior based on rheological characteristics. Barite sag may be described by the Stokes flow regime, an extreme case of laminar flow where viscous effects are much greater than inertial forces. For Stokes flow regime, the drag force on a spherical particle in a Newtonian fluid is balanced by the net gravitational force acting on the sphere. Therefore, in Equation 1 the gravitational force is equal to the drag force.

$$(4/3)*\pi*a^3*(\rho_s-\rho_f)*g=6*\pi*\eta*a*U \qquad \text{Eq. 1}$$

In Equation 1, a is the radius of the spherical particle, $\eta$ is fluid viscosity, and $\rho_s$ and $\rho_f$ are densities of the particle and surrounding fluid respectively and g is the acceleration due to gravity. U is the rate of sedimentation (terminal settling velocity), which is the vertical velocity of the particle that is reached when drag force and gravity force are equal, so that velocity no longer changes. U is the particle sedimentation rate rate.

For non-Newtonian fluids, Equation 1 may be modified to account for pseudo-plastic and/or visco-plastic effects; shear thinning or thickening, yield stress, time-dependent viscosity. For example, Atapattu et al., "*Creeping sphere motion in Herschel-Bulkley fluids*" (1995) suggested an additional term in Equation 1 for particle sedimentation in Herschel-Bulkley (H-B) type of fluids. However, his model was applicable for particles settling in quiescent fluids, i.e. no external shear. The oil-based drilling fluids may be well categorized as Herschel-Bulkley; however, the term provided by Atapattu required modification to capture the external shear effect on sedimentation in drilling fluids. The term is modified (based on scaling analysis) and included in Equation 2.

$$(4/3)*\rho*a_i^3*(\rho_s-\rho_f)*g = 6*\pi*a_i*U_i*(\mu+k*(\tau_0^{HB})^{1/n})$$
$$\text{or } U_i = [(4/3)*\pi*a_i^3*(\rho_s-\rho_f)*g]/[6*\pi*a_i(\mu+k*(\tau_0^{HB})^{1/n})] \quad \text{Eq. 2.}$$

$$U_{avg} = \Sigma \Psi_i U_i \quad \text{Eq. 3}$$

In Equation 2, $\tau_0^{HB}$ and n are the yield stress and shear thinning index, respectively, obtained from Herschel-Bulkley modeling of the viscometer/rheometer data. The parameter $\mu$ denotes the viscosity of the drilling fluid under external shear rate $\gamma$. The Rheological properties $\tau_0^{HB}$, n and $\mu$ are strongly dependent on temperature (T) and pressure (P) and the data obtained at desired temperature and pressure conditions. The parameter k is an empirical constant that ranges between 0.1 to 10. t. The average settling rate of the wide range of particle size distribution of barite is taken into account by summing up the product of particle sedimentation speed ($U_i$) and the weight fraction ($\Psi_i$) of the particle size $a_i$ in the particle size distribution as ($\Sigma \Psi_i U_i$).

The density value for the particle, $\rho_s$, is considered to be 4.2 g/cc for Barite. The density of the surrounding fluid, $\rho_f$, is determined by the base oil type. The shear rate, $\gamma$, can be a low shear rate selected to model the conditions in wellbore that cause sag and to match the shear rpm of the viscometer/rheometer; for instance, the shear rate may be 5 s$^{-1}$. The unknown values, viscosity, yield stress, and shear thinning index, are the rheological properties used to predict the sag rate. Viscosity can be determined by a viscometer/rheometer at an rpm to match the shear rate. Yield stress and shear thinning index are determined by a viscometer/rheometer at multiple rpm settings, which results are then run through Halliburton DFG software to give numbers for yield stress and shear thinning index. All the fluid properties are measured at, or adjusted to, the same temperature and pressure.

Example 1 below explains how the empirical constant k was determined and how Equation 2 can be used to give sag rate predictions that match the sag rate given by DHAST.

In addition to shear stress and/or viscosity data from a viscometer/rheometer, the visco-elastic data may be obtained from a rheometer at desired conditions of temperature (T) and pressure (P). The visco-elastic data may be in terms of first Normal stress difference, second normal stress difference, primary normal stress coefficient, second normal stress coefficient, elongational viscosity, the dimentionless visco-elastic parameters including Maxwellian relaxation time, Deborah number, Weissenberg number, elasticity number and the like.

The Rheological properties of the fluid that comprise of Rheological data and/or the characteristics parameters obtained by applying one or more of above pseudo-plastic/visco-plastic models and/or the above obtained visco-elastic properties are used in a equation to predict the sag rate behavior.

In another embodiment, the method includes the steps of measuring viscosity of the fluid surrounding the weighting material and visco-elastic properties that may comprise of first Normal stress difference of a drilling fluid using a viscometer/rheometer and a rheometer, respectively, and determining the dynamic sag rate via an equation that quantitatively establishes the relationship between those rheological parameters and sag rate. The viscometer/rheometer can be any known in the art, especially those that can be used at drilling sites. Non-limiting examples of possible viscometers/rheometers include the fann 35, fann 75, and fann 77. Other possible instruments can include the Anton Paar rheometer. The equation can be Equation 3, which is described below.

Equation 1 can be modified by taking into account for visco-elastic effect the of the drilling fluid. The drag on a sphere in visco-elastic fluids is determined by a complex interplay between the shear and extensional rheological characteristics of the system. In highly visco-elastic fluids, drag enhancement has been observed experimentally by many researchers. As an example, US Patent publication (US 2011/0219856) A1 suggested the following equation to qualitatively capture the sedimentation in visco-elastic fluids.

$$(4/3)*\pi*a^3*(\rho_s-\rho_f)*g = 6*\pi*\eta*a*U+\alpha*4*\pi*a^2*N_1 \quad \text{Eq. 4.}$$

In Equation 4, $N_1$ is the first Normal stress difference of the fluid under steady shear. The term $\eta$ in the viscous drag term represents the viscosity of the fluid surrounding the settling particle. The Rheological properties $\eta$ and $N_1$ are strongly dependent on shear rate ($\gamma$), temperature (T) and pressure (P) and the data obtained at desired shear, temperature and pressure conditions.

The fluid viscosity surrounding the barite particle, that is the viscosity of the drilling fluid without barite, may be obtained by formulating the given drilling fluid without barite and collecting viscosity data at desired shear rates. As an alternative, to obtain drilling fluid viscosity without barite, at say the shear rate of 3 RPM on fann-35, following method could be used; the shear stress term, [⊖3 rpm] (the fann-35 3 RPM dial reading), can be divided by the Thomas effect term (Qin and Fan, *Materials Science and Technology*, 2011) to obtain [⊖3 rpm]$^{fluid\_wb}$ i.e. the shear stress of the drilling fluid in the absence of barite particle as shown below in Equation 5($\phi$ is barite volume fraction). The resultant value for $\eta$ can then be used in Equation 4.

$$[\ominus 3 \text{ rpm}]^{fluid\_wb} = (\ominus 3 \text{ rpm})/(1+2.5*\phi+A*\phi^2+B*\exp(C*\phi)) \quad \eta = [\ominus 3 \text{ rpm}]^{fluid\_wb}/\gamma, \text{ where } \gamma \sim 5s^{-1} \quad \text{Eq. 5.}$$

Equation 4 can be further modified to include a non-linear dependence on $|N_1|$ which may better characterize quantitatively the nature of the relation between sedimentation and fluid elasticity. The non-linear dependence is captured by the parameter $\beta$ in Equation 6.

$$(4/3)*\pi*a^3*(\rho_s-\rho_f)*g = 6*\pi*\eta*a*U+\alpha*4*\pi*a^2*|N_1|^\beta$$
$$\text{or } U = [(4/3)*\pi*a^3*(\rho_s-\rho_f)*g-\alpha*4*\pi*a^2*|N_1|^\beta]/(6*\pi*\eta*a) \quad \text{Eq. 6.}$$

The terms $\alpha$ and $\beta$ are empirical constants. The term $\beta$ is 0.75 where $\alpha$ ranges from 0.0001 to 0.1. As for Equation 6, a is the average radius of the barite particle, and the density of barite particle, $\rho_s$, is considered to be 4.2 g/cc. The density of the surrounding fluid, $\rho_f$, is determined by the base oil type. The shear rate, $\gamma$, can be a low shear rate selected to model the conditions in wellbore that cause sag and to match the shear rpm of the viscometer/rheometer. Note that the rheological parameters, fluid viscosity ($\eta$) and $N_1$ are dependent on the shear rate $\gamma$ applied to the fluid, and hence the sedimentation rate also becomes dependent on the rate at which fluid is being sheared. Fluid viscosity can be determined using a viscometer/rheometer at an rpm to match the shear rate. The first Normal stress difference $N_1$ can be obtained using a rheometer. All fluid properties must be measured at, or adjusted to, the same temperature and pressure. Example 2 below explains how the empirical constants α and β were determined and demonstrates the use of Equation 6 to predict sag rate based on rheological characteristics.

The following examples illustrate possible embodiments of the present invention but are intended to be in no way limiting of the scope of the invention.

EXAMPLE 1

Equation 2 was used as a basis to model the sag behavior in various oil-based drilling fluids. The relationship can quantitatively predict dynamic sag using the rheology data as input.

To obtain the empirical constant k in the model, experimental data was gathered on various oil-based drilling fluids at desired temperature, pressure and shear rate conditions. The experimental data included viscosity (η) data from fann-35 (or fann-75/77) and sag rates (U) from DHAST.

The oil-based drilling fluids were chosen such as to have a variation in the base oil type, oil/water (o/w) ratio, low gravity solids content, viscosifier concentration and mud weight. After preparation, the drilling fluids were hot-rolled at the selected temperature for 16 hours before performing testing.

The viscosity data was measured at 3 rpm (5 s$^{-1}$), 150° F. and atmospheric pressure. A fann-35 was used to evaluate the data at 150° F. while a fann-75/77 was used at temperatures greater than 150° F. The fluid samples were also tested on the fann-35 viscometer/rheometer for stress measurements (or dial readings) at 600, 300, 200, 100, 6 and 3 rpm rotational speeds, from which the Herschel-Bulkley parameters ($\tau_0^{HB}$ and n, for yield stress and shear thinning index, respectively) are calculated using Halliburton DFG software. The DHAST experiments were performed at temperature of 150° F. and pressure 2000 psi and under a shear rate of about 5 s$^{-1}$, the shear rate is similar to that obtained at 3 rpm on fann35. The sag rate averaged for the first three hours was used for modeling purposes.

Table 1 shows the fann 35 viscometer/rheometer reading (⊖3 rpm), yield stress ($\tau_0^{HB}$), and shear thinning index (n) for some drilling fluids samples. The viscosity μ is obtained as ([⊖3 rpm]/γ).

TABLE 1

Rheological (viscous and visco-plastic) properties of different mud weight fluid samples (150° F., typical - barite sample).

| Fluid sample No. | Base oil | Oil/Water Ratio | Mud Weight | fann-35 ⊖ 3 rpm (γ ~5 s$^{-1}$) | $\tau_0^{HB}$ (from DFG) | n (from DFG) |
|---|---|---|---|---|---|---|
| #1 | Baroid Alkane ™ (BA) | 65/35 | 12 | 13 | 12.4 | 0.77 |
| #2 | BA | 65/35 | 12 | 8 | 8.00 | 0.79 |
| #3 | BA | 80/20 | 12 | 9 | 9.32 | 0.88 |
| #4 | BA | 90/10 | 12 | 7 | 7.29 | 1.05 |
| #5 | ESCAID 110 | 65/35 | 12 | 13 | 13.01 | 0.91 |
| #6 | ESCAID 110 | 75/25 | 12 | 8 | 8.21 | 0.89 |
| #7 | ESCAID 110 | 75/25 | 12 | 11 | 10.70 | 0.87 |
| #8 | BA | 75/25 | 12 | 10 | 10.05 | 0.83 |
| #9 | BA | 80/20 | 14.5 | 15 | 14.50 | 0.80 |
| #10 | BA | 80/20 | 10 | 6 | 5.63 | 1.01 |
| #11 | BA | 90/10 | 14.5 | 16 | 16.86 | 0.98 |
| #12 | BA | 75/25 | 10 | 6 | 5.95 | 0.80 |

TABLE 1-continued

Rheological (viscous and visco-plastic) properties of different mud weight fluid samples (150° F., typical - barite sample).

| Fluid sample No. | Base oil | Oil/Water Ratio | Mud Weight | fann-35 ⊖ 3 rpm (γ ~5 s$^{-1}$) | $\tau_0^{HB}$ (from DFG) | n (from DFG) |
|---|---|---|---|---|---|---|
| #13 | BA | 75/25 | 14.5 | 21 | 19.45 | 0.79 |
| #14 | BA | 65/35 | 10 | 4 | 4.12 | 0.77 |

The averaged value of k obtained by incorporating the rheology and experimental sag rate data (from DHAST) of 14 selected drilling fluids into Equations 2 and 3 is about k=0.18.

Using this empirical constant, the model (Equations 2 and 3) was used to predict sag rates based on the rheology data.

FIG. 1 shows a plot of sag rate predicted by the model (Equations 2 and 3) versus experimental sag as determined by DHAST for above 14 selected drilling fluids. The RMSE (Root Mean Square Error) between the predicted and measured values of sag rates (U) is only around 0.55 mm/hr; this error is similar to the instrumental error expected for the DHAST instrument.

In order to check the validity of the model, Equations 2 and 3 were used to predict the sag rate of drilling fluids not used for building the model parameters, and then compared to DHAST results of the respective drilling fluids. Drilling fluids with variation in Particle size distribution (PSD), field based muds, and drilling fluids with variation in temperature condition were tested. Table 2 shows rheology data, and predicted and experimental sag rate for two drilling fluids varying in barite particle size distribution (PSD). Table 3 shows rheology data, and predicted and experimental sag rate for two different field based drilling fluids. Table 4 shows rheology data, and predicted and experimental sag rate for drilling fluids that vary in temperature.

TABLE 2

Predicted versus experimental sag rate for drilling fluids with variation in PSD.

| Fluid Sample No. | Barite type | fann-35 ⊖ 3 rpm (γ ~5 s$^{-1}$) | $\tau_0^{HB}$ (from DFG) | n (from DFG) | Predicted U (mm/hr) | Experimental U (mm/hr) (γ ~5 s$^{-1}$) |
|---|---|---|---|---|---|---|
| #15 | Large | 7 | 7.16 | 0.85 | 17.72 | 18.3 |
| #16 | Extra-fine | 11.5 | 11.5 | 0.77 | 0.1 | 0.47 |

TABLE 3

Predicted versus experimental sag rate for field based drilling fluids.

| Fluid Type | Mud weight | fann-35 ⊖ 3 rpm | $\tau_0^{HB}$ (from DFG) | n (from DFG) | Predicted U (mm/hr) | Experimental U (mm/hr) (γ ~5 s$^{-1}$) |
|---|---|---|---|---|---|---|
| Field Mud A | 12.3 | 5 | 5.07 | 0.84 | 7.6 | 6.2 |
| Field Mud B | 11.7 | 6 | 6.07 | 0.82 | 6.1 | 5.4 |

TABLE 4

Predicted versus experimental sag rate for drilling fluids of various temperatures.

| Fluid Sample No. | Temperature (° F.) | fann-77 ⊖ 3 rpm (γ ~5 s$^{-1}$) | $\tau_0^{HB}$ (from DFG) | n (from DFG) | Predicted U (mm/hr) | Experimental U (mm/hr) (γ ~5 s$^{-1}$) |
|---|---|---|---|---|---|---|
| #17 | 150 | 13  | 12.4 | 0.77 | 2.5 | 2.8 |
| #17 | 200 | 9   | 7.17 | 0.59 | 3.2 | 3.1 |
| #17 | 250 | 8.3 | 5.4  | 0.50 | 3.7 | 3.5 |
| #17 | 300 | 6.9 | 6.31 | 0.68 | 4.8 | 5.2 |

The predicted sag rates from the fluids of Table 2, 3, and 4 correspond with the experimental sag rates with a RMSE of less than 0.6 mm/hr. Thus, the sag predictions made according to this method can act as alternative to lab-based DHAST tests, saving significant amount of time and cost. The prediction method may also be used on the field to evaluate sag potential of the drilling fluid under desired conditions of temperature, pressure and shear rate conditions.

EXAMPLE 2

Equation 6 was used as a basis to model the sag behavior in various oil-based drilling fluids. The relationship can quantitatively predict dynamic sag using the rheology data as input. The experimental data to obtain empirical constants in Equation 6 included viscosity (η) data from fann-35, fluid elasticity or first Normal stress difference data ($N_1$) from an Anton Paar Rheometer, and sag rates (U) from DHAST.

The oil-based drilling fluids were formulated such as to have a variation in the base oil type, o/w ratio, additive concentration and mud weight. The low gravity solids content and viscosifier concentration were also varied to obtain differentiation in terms of low-end rheology. After preparation, the drilling fluids were hot-rolled at 150° F. for 16 hours before testing.

The viscosity data was measured at 150° F. and atmospheric pressure.

The magnitude of $N_1$ is a measure of the degree of visco-elasticity of the fluid under shear. Using the Anton Paar Rheometer (MCR-301), parallel plate geometry PP-50 was used to study the rotational rheology of the drilling fluid. The gap between the parallel plates was chosen to be 1 mm so that the gap size remains significantly higher than the barite particle size. All tests were conducted at 150° F. and atmospheric pressure. The drilling fluid (after hot-rolling) was mixed in the fann multi-mixer for about 10 minutes and then added between the parallel plates of the PP-50 geometry (~2 ml). The drilling fluid was pre-sheared between the plates for 1 min at a shear rate of 10 s$^{-1}$. Then, the drilling fluid was subjected to shear ramp starting from 0.1 s$^{-1}$ to a maximum shear rate of 50 s$^{-1}$ with 50 data points collected at each of the selected intermediate shear rates. The shear and normal stress response was recorded for every data point.

For a visco-inelastic fluid, $N_1 \sim 0$. For a viscoelastic fluid under flow, normal stresses in velocity and velocity gradient directions, $\tau_{xx}$ and $\tau_{yy}$ respectively, may become unequal and therefore, $N_1 = \tau_{xx} - \tau_{yy}$ becomes non-zero. When $N_1$ is measured with parallel plate geometry of a Rheometer, the negative value of $N_1$ implies that the Rheometer plates are pulled together, as observed in the present study. For the sag modeling purpose, the magnitude of $N_1$ which is expressed as $|N_1|$ to represent the degree of fluid-elasticity.

The DHAST experiments were done at a shear rate of about 5 s$^{-1}$. The sag rate obtained in the first three hours after warm-up was considered for the purpose of modeling.

Table 5 shows the viscometer/rheometer reading, first Normal stress difference, and experimental sag rate for eight different drilling fluids.

TABLE 5

Rheology (viscosity and visco-elasticity) and sag rates for various drilling fluids at 150° F.

| Drilling Fluid | fann-35 ⊖ 3 rpm (γ ~5 s$^{-1}$) | $|N_1|$ (Pa) (γ ~5 s$^{-1}$) | Experimental U (mm/hr) (γ ~5 s$^{-1}$) |
|---|---|---|---|
| #I    | 10 | 130 | 4.71 |
| #II   | 6  | 235 | 5.55 |
| #III  | 15 | 110 | 4.31 |
| #IV   | 13 | 325 | 2.48 |
| #V    | 8  | 244 | 3.78 |
| #VI   | 11 | 233 | 3.43 |
| #VII  | 7  | 240 | 3.8  |
| #VIII | 11 | 150 | 3.93 |

The fann-35 3 RPM dial reading, ⊖3 rpm, represents the shear stress of a drilling fluid, which is tabulated in Table 5 for the selected fluids. Equation 5 was used to determine the term η, the viscosity of the fluid surrounding the settling particle.

The data for η, $|N_1|$ and sag rate U for the different drilling fluids listed in Table 5 was incorporated into Equation 6. The average particle radius is considered as a=12.5 μm, which is standard API average size ($d_{50}$) of the barite particle. The barite density $\rho_s$, is considered to be 4.2 g/cc and the fluid density $\rho_f$ is incorporated as per as the base oil (for instance, Baroid ALKANE™, ESCAID, and ENCORE® BASE) being used. Using these input data, Equation 6 was solved to empirically obtain values of the constants α and β. The most consistent fitting obtained for β was 0.75 where α was 0.00126±0.0002.

Figure 2:
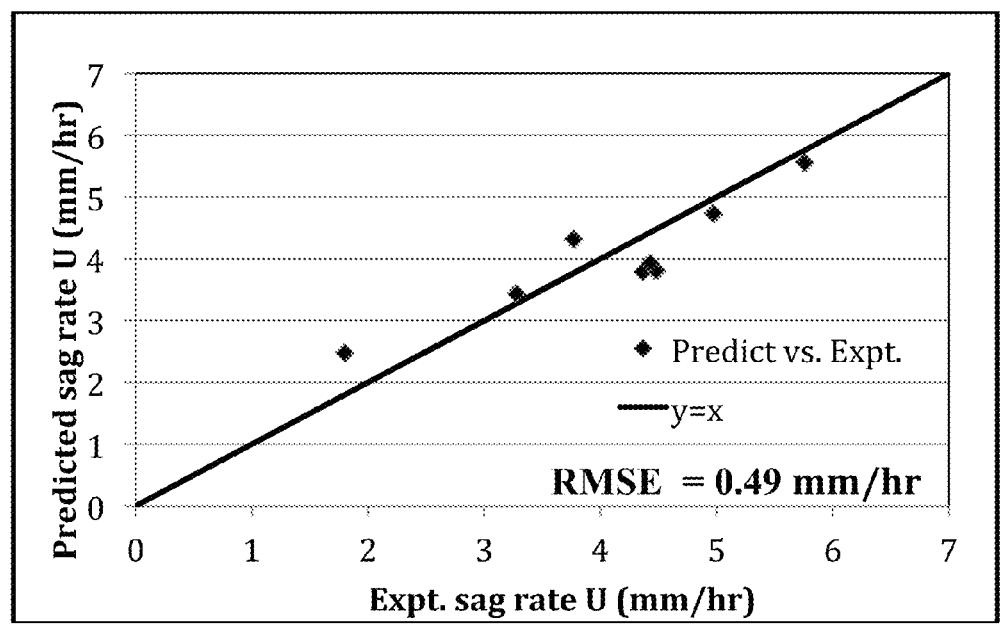
FIG. 2 is a plot of sag rate predicted by Equation 5 versus experimental sag as determined by DHAST, for various drilling fluids.

After determining the empirical constants, fluid rheology (η and $N_1$) was used in Equation 6 to predict sag rate (U). FIG. 2 shows a plot of sag rate predicted by Equation 6 versus experimental sag as determined by DHAST for the eight selected fluids in Table 5. The sag rate predictions were in agreement with corresponding experimental sag rates. The RMSE (Root Mean Square Error) between the predicted and measured values of sag rates (U) was around 0.49 mm/hr; this error is similar to the instrumental error expected for the DHAST equipment.

In order to check the validity of the model, Equation 2 was used to predict the sag rate of drilling fluids not used for building the model parameters, and then compared to DHAST results of the respective drilling fluids. Table 6 shows rheology data, and predicted and experimental sag rate for four drilling fluids varying in formulation.

TABLE 6

Experimental versus predicted sag rate for various drilling fluids at 150° F.

| Mud No. | O/W ratio | fann⊖ 3 rpm (γ ~5 s$^{-1}$) | fann ⊖ 3 rpm$^{fluid\_wb}$ | $|N_1|$ (Pa) (γ ~5 s$^{-1}$) | Predicted U (mm/hr) | Expt U (mm/hr) (γ ~5 s$^{-1}$) |
|---|---|---|---|---|---|---|
| #IX  | 75/25 | 6  | 4.17 | 160 | 5.96 | 5.08 |
| #X   | 75/25 | 20 | 6.98 | 280 | 2.29 | 2.83 |
| #XI  | 65/35 | 5  | 3.45 | 210 | 6.09 | 5.92 |
| #XII | 65/35 | 15 | 5.11 | 400 | 1.57 | 1.05 |

The predicted sag rates (U) correspond to the experimental sag rates as determined by DHAST with a RMSE of 0.59 mm/hr. Thus, the sag rate behavior of drilling fluids can be predicted by the sag model using rheological parameters as input.

Although the invention is primarily directed toward the measurement of barite sag in drilling fluids, the methods disclosed herein can be used to determine the sag of rate any particulate suspended in any type of fluid. Examples include any particulate laden fluid that exhibits particle sag or settling tendencies such as cementing fluids, spacer fluids, fracturing fluids and gravel pack fluids.

The various embodiments of the present invention can be joined in combination with other embodiments of the invention and the listed embodiments herein are not meant to limit the invention. All combinations of various embodiments of the invention are enabled, even if not given in a particular example herein.

While illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method comprising:
    measuring rheological data for a plurality of fluids having particulates suspended therein, wherein the rheological data is selected from the group consisting of: a shear stress, a yield stress, a viscosity, a shear-thinning index, and any combination thereof;
    applying a pseudo-plastic model and a visco-plastic model to the rheological data to produce characteristic parameters for each of the plurality of fluids;
    applying the characteristic parameters for each of the plurality of fluids to an equation to predict a dynamic sag rate for each of the plurality of fluids, wherein the equation is: $(4/3)*\pi*a_i^3*(\rho_s-\rho_f)*g=6*\pi*a_i*U_i*(\mu+k*(T_0^{HB})^{1/n})$. wherein $a_i$, is a radius of the particulates, $\rho_s$ is a density of the particulates, $\rho_f$ is a density of the fluid surrounding the particulates, g is acceleration due to gravity, $U_i$ is the dynamic sag rate of particulates of size $a_i$, $\mu$ is a viscosity of the fluid, $\gamma$ is a shear rate, k is an empirical constant that ranges from 0.01 to 10, $T_0^{HB}$ is a yield stress, and n is a shear thinning index; and
    formulating a drilling fluid based on the dynamic sag rate for each of the plurality of fluids so as to minimize sag in the drilling fluid.

2. The method of claim 1 further comprising: drilling a wellbore with the drilling fluid.

3. The method of claim 1, wherein measuring rheological data is performed at a shear rate of 5 $s^{-1}$.

4. The method of claim 1, wherein the pseudo-plastic model is selected from the group consisting of a power-law model, an Eyring model, a Cross model, a Carreau model, an Ellis model, and any combination thereof.

5. The method of claim 1, wherein the visco-plastic model is selected from the group consisting of a Bingham-plastic model, a Casson model, a Herschel-Bulkley model, and any combination thereof.

6. A method comprising:
    measuring rheological data for a plurality of fluids having particulates suspended therein, wherein the rheological data is selected from the group consisting of: a shear stress, a yield stress, a viscosity, a shear-thinning index, and any combination thereof;
    applying a pseudo-plastic model and a visco-plastic model to the rheological data to produce characteristic parameters for each of the plurality of fluids;
    applying the characteristic parameters for each of the plurality of fluids to an equation to predict a dynamic sag rate for each of the plurality of fluids, wherein the equation is: $(4/3)*\pi*a_i^3*(\rho_s-\rho_f)*g=6*\pi*a_i*U_i*(\mu+k*(T_0^{HB})^{1/n})$ wherein $a_i$, is a radius of the particulates, $\rho_s$ is a density of the particulates, $\rho_f$ is a density of the fluid surrounding the particulates, g is acceleration due to gravity, $U_i$ is the dynamic sag rate of particulates of size $a_i$, $\mu$ is a viscosity of the fluid, $\gamma$ is a shear rate, k is an empirical constant that ranges from 0.01 to 10, $T_0^{HB}$ is a yield stress, and n is a shear thinning index; and
    adjusting a drilling fluid composition based on the dynamic sag rate for each of the plurality of fluids so as to minimize sag in the drilling fluid.

\* \* \* \* \*